(12) United States Patent
Kotelko et al.

(10) Patent No.: US 7,927,491 B2
(45) Date of Patent: Apr. 19, 2011

(54) INTEGRATED BIO-DIGESTION FACILITY

(75) Inventors: Mike Kotelko, Vegreville (CA); Tevor Jason Nickel, Hairy Hill (CA); Bern Kotelko, Vegreville (CA); Brett Kotelko, Edmonton (CA); Xiaomei Li, Edmonton (CA)

(73) Assignee: Highmark Renewables Research Limited Partnership, Vegreville, Alberta (CA)

( * ) Notice: Subject to any disclaimer, the term of this patent is extended or adjusted under 35 U.S.C. 154(b) by 270 days.

(21) Appl. No.: 12/004,927

(22) Filed: Dec. 21, 2007

(65) Prior Publication Data

US 2009/0250401 A1    Oct. 8, 2009

(51) Int. Cl.
*C02F 3/32* (2006.01)
*C02F 3/28* (2006.01)
*C02F 11/04* (2006.01)

(52) U.S. Cl. ........ 210/602; 210/603; 210/614; 210/259; 71/10; 71/15; 71/21

(58) Field of Classification Search ................. 210/603, 210/614, 602, 252, 259; 71/10, 15, 21
See application file for complete search history.

(56) References Cited

U.S. PATENT DOCUMENTS

| | | | |
|---|---|---|---|
| 1,999,973 A | 4/1935 | Genter et al. | |
| 2,188,847 A | 1/1940 | Streander | |
| 2,903,131 A | 9/1959 | Heinrichs | |
| 3,226,317 A * | 12/1965 | Albertson | 210/609 |
| 3,296,122 A | 1/1967 | Karassik et al. | |
| 3,440,166 A | 4/1969 | Davis et al. | |
| 3,824,185 A | 7/1974 | Caldwell et al. | |
| 4,067,801 A * | 1/1978 | Ishida et al. | 210/603 |
| 4,076,515 A | 2/1978 | Rickard et al. | |
| 4,204,842 A | 5/1980 | Morel et al. | |
| 4,303,412 A | 12/1981 | Baikoff | |
| 4,354,936 A * | 10/1982 | Ishida et al. | 210/602 |
| 4,366,059 A | 12/1982 | Witt et al. | |
| 4,400,195 A | 8/1983 | Rijkens | |
| 4,415,453 A | 11/1983 | Witt et al. | |
| 4,577,996 A | 3/1986 | Elias et al. | |
| 4,750,454 A | 6/1988 | Santina et al. | |

(Continued)

FOREIGN PATENT DOCUMENTS

CA    2248588    9/1997

(Continued)

OTHER PUBLICATIONS

Pratt, Shelia, "Good, old-fashioned manure is province's new black gold. Breakthrough biorefinery near Vegreville, a working carbon market set new standards", The Edmonton Journal, www.edmontonjournal.com/story_print.html?id=1266220&sponsor=, Feb. 8, 2009.

(Continued)

*Primary Examiner* — Fred Prince
(74) *Attorney, Agent, or Firm* — McCarter & English, LLP; Maria Laccotripe Zacharakis; Yu Lu

(57) ABSTRACT

Methods and systems for processing organic waste material are provided. These methods and systems include integrating an anaerobic bio-digester and nutrient recovery module with a bio-production facility, which can locally provide feedstock for the bio-production facility, and can locally provide organic material for the anaerobic bio-digester. Methods and systems for integrating an anaerobic bio-digester with a gas cleaner are also provided, which can recover nutrients while cleaning the biogas produced by the anaerobic bio-digester.

107 Claims, 4 Drawing Sheets

U.S. PATENT DOCUMENTS

| | | | |
|---|---|---|---|
| 4,765,900 | A | 8/1988 | Schwoyer et al. |
| 5,070,016 | A | 12/1991 | Hallberg |
| 5,297,741 | A | 3/1994 | Zurn et al. |
| 5,337,965 | A | 8/1994 | Chiovitti |
| 5,360,546 | A | 11/1994 | Tomita et al. |
| 5,378,322 | A | 1/1995 | Hornsey et al. |
| 5,476,994 | A | 12/1995 | Trezek |
| 5,478,473 | A | 12/1995 | Oshima |
| 5,607,060 | A | 3/1997 | Fristad et al. |
| 5,635,394 | A | 6/1997 | Horn et al. |
| 5,725,770 | A | 3/1998 | Henry et al. |
| 5,762,449 | A | 6/1998 | Hey |
| 5,851,398 | A | 12/1998 | Adey et al. |
| 5,869,323 | A | 2/1999 | Horn et al. |
| 5,993,503 | A | 11/1999 | Kruidhof et al. |
| 6,036,862 | A * | 3/2000 | Stover ............................ 210/603 |
| 6,059,972 | A * | 5/2000 | Mahrer .......................... 210/603 |
| 6,136,590 | A | 10/2000 | Kruse |
| 6,221,254 | B1 | 4/2001 | Dickerson et al. |
| 6,296,766 | B1 * | 10/2001 | Breckenridge ................ 210/613 |
| 6,299,774 | B1 | 10/2001 | Ainsworth et al. |
| 6,342,378 | B1 | 1/2002 | Zhang et al. |
| 6,355,456 | B1 | 3/2002 | Hallberg et al. |
| 6,368,849 | B1 | 4/2002 | Norddahl et al. |
| 6,403,364 | B1 | 6/2002 | Hince |
| 6,409,788 | B1 | 6/2002 | Sower et al. |
| 6,423,532 | B1 | 7/2002 | Rindelaub |
| 6,464,875 | B1 | 10/2002 | Woodruff et al. |
| 6,497,741 | B2 | 12/2002 | Sower et al. |
| 6,508,078 | B2 | 1/2003 | Sower et al. |
| 6,521,129 | B1 * | 2/2003 | Stamper et al. ............... 210/603 |
| 6,623,640 | B2 * | 9/2003 | Lanting et al. ................ 210/603 |
| 7,005,068 | B2 * | 2/2006 | Hoffland ....................... 210/603 |
| 7,014,768 | B2 | 3/2006 | Li et al. |
| 7,381,550 | B2 | 6/2008 | Hallberg et al. |
| 2002/0092799 | A1 | 7/2002 | Storruste |
| 2003/0038078 | A1 | 2/2003 | Stamper et al. |
| 2003/0038079 | A1 | 2/2003 | Miller et al. |
| 2003/0116511 | A1 | 6/2003 | Dias |
| 2004/0164021 | A1 | 8/2004 | Li et al. |
| 2006/0115884 | A1 | 6/2006 | Burmaster |
| 2007/0000835 | A1 * | 1/2007 | Gordon ......................... 210/603 |
| 2007/0199894 | A1 | 8/2007 | Peyton et al. |
| 2007/0249029 | A1 * | 10/2007 | Marshall et al. .............. 435/161 |
| 2009/0014950 | A1 | 1/2009 | Mizutani et al. |
| 2009/0127092 | A1 | 5/2009 | Tedder |
| 2009/0206028 | A1 | 8/2009 | Jiang et al. |
| 2009/0209014 | A1 | 8/2009 | Chi et al. |
| 2009/0250401 | A1 | 10/2009 | Kotelko et al. |
| 2009/0325253 | A1 * | 12/2009 | Ascon et al. .................. 435/163 |

FOREIGN PATENT DOCUMENTS

| | | |
|---|---|---|
| CA | 2259673 | 7/2000 |
| CA | 2376366 | 9/2003 |
| EP | 1320388 B1 | 6/2003 |
| EP | 1 354 940 | 10/2003 |
| GB | 2301112 A | 11/1996 |
| JP | 60-41593 A * | 3/1985 |
| JP | 10235317 | 9/1998 |
| JP | 2000016229 | 1/2000 |
| WO | 9323170 A1 | 11/1993 |
| WO | WO-93/23170 A1 | 11/1993 |
| WO | WO 99/42423 | 8/1999 |
| WO | WO 00/53542 | 9/2000 |
| WO | WO 02/15945 | 2/2002 |
| WO | 2009090476 A2 | 7/2009 |

OTHER PUBLICATIONS

Pratt, Shelia, "Virtuous' power. Cattle manure and Alberta ingenuity are combining to produce a fledgling alternative energy economy", The Edmonton Journal, www.edmontonjournal.com/story_print.html?id=1266353&sponsor=, Feb. 9, 2009.
The Edmonton Journal, "Use of manure power improves ethanol plant's carbon footprint", www.edmontonjournal.com/story_print.html?id=1266359&sponsor=; Feb. 8, 2009.
Li, Science and My Life—Searching for Happiness, oral slide presentation at Shan'xi Agricultural University, Shan'xi Province, P. R. China, on Nov. 28, 2003 (irrelevant slides redacted / deleted).
Li, an oral slide presentation at Lakeland College, Alberta, Canada, on Sep. 9, 2003 (irrelevant slides redacted / deleted).
Zeng et al., Feasibility Study of Air Stripping of Ammonia from Digested Cattle Manure, ADSW Conference proceedings, vol. 1—Session 8b: Economical Evaluation. 2005.
Zeng et al., Nutrient Removal from Anaerobically Digested Cattle Manure by Struvite Precipitation. J. Environ. Eng. Sci. 5: 285-294, 2006.
Guo et al., Removal of Ammonium and Potassium from RO Premeate of Anaerobically Digested Cattle Manure by Natural Zeolite. Presentation at the CSBE/SCGAB 2006 Annual Conference at Edmonton, Alberta, 2006.
Integrated On-Farm Food/Energy System (Columbia, MO) Slide (author unknown), 1974.
Baker et al. Safety and Health Considerations on an Integrated Energy Farm (summary). Presentation at the Mid-Central Region American Society of Agricultural Engineers. 1984.
Stahl et al., An Internal Combustion Engine Fueled with Biogas Integrated into an Ethanol Plant (summary). Presentation at the 1981 Mid-Central Meeting American Society of Agricultural Engineers, 1981.
Farm Gets Energy from Manure (author unknown). Missouri Farm News Science. vol. 74. No. 6, 1982.
Fischer et al., Bioconversion of Animal Manure into Electricity and a Liquid Fuel. Biotechnology and Bioengineering Sym. 13: 527-538, 1983.
Lau et al., Ethanolic fermentation of hydrolysates from ammonia fiber expansion (AFEX) treated corn stover and distillers grain without detoxification and external nutrient supplementation. Biotechnology and Bioengineering 99(3): 529-539, 2007 [published on-line on Aug. 17, 2007].
Khan et al., Bioethanol production from dilute feedstock. Bioresource Technology 47: 29-36, 1994.
Sommer et al., Potential for using thermophilic anaerobic bacteria for bioethanol production from hemicellulose. Biochemical Society Transactions 32(pt. 2): 283-289, 2004.
Mohagheghi et al., Impact of recycling stillage on conversion of dilute sulfuric acid pretreated corn stover to ethanol. Biotechnology and Bioengineering, 2010 [published on-line on Dec. 7, 2009].
Zhengbo et al. A sustainable pathway of cellulosic ethanol production integrating anaerobic digestion with biorefining. Biotechnology and Bioengineering. 2010. [published on-line on Dec. 7, 2009].
International Search Report and Written Opinion of PCT/CA2009/001575, mailed on Jan. 25, 2010.
Bowlby, E., et al. Removal of infectivity of infectious laryngotracheitis virus (ILTV) using thermophilic anaerobic digestion (TAD) process. The Animal Health Forum, FSD, ARD, 14(2):3, Dec. 2009.
Saunders, O., et al. Pathogen Reduction in Anaerobic Digestion of Manure. Cornell University Cooperative Extension. Available online at http://www.extension.org/pages/Pathogen_Reduction_in_Anaerobic_Digestion_of_Manure. Last updated on Sep. 29, 2010.
Pratt, Sheila, "Good, old-fashioned manure is province's new black gold. Breakthrough biorefinery near Vegreville, a working carbon market set new standards", The Edmonton Journal, www.edmontonjournal.com/story.sub.—print.html?id=1266220 &sponser=, Feb. 8, 2009.
Pratt, Sheila, "Virtuous' power. Cattle manure and Alberta ingenuity are combining to produce a fledging alternative energy economy", The Edmonton Journal, www.edmontonjournal.com/story.sub.—print.html?id=1266353&sponsor=, Feb. 9, 2009.
The Edmonton Journal, "Use of manure power improves ethanol plant's carbon footprint", www.edmontonjournal.com/story.sub.—print.html?id=1266359&sponsor=; Feb. 8, 2009.

* cited by examiner

INTEGRATED BIO-DIGESTION FACILITY

BACKGROUND OF THE INVENTION

The present invention relates to methods and systems of processing organic waste material.

Organic waste material, such as municipal wastewater or livestock manure, can present problems when generated on a large scale. Organic waste material can be a health risk and a nuisance. Decomposing organic waste can also release greenhouse gases, such as methane and carbon dioxide, and can be a source of air and water pollution. Strategies for dealing with organic waste in large qualities are therefore needed.

Organic waste material can be converted into useful products or can have useful products extracted from it. This conversion can be done within waste conversion facilities, such as, for example, an anaerobic bio-digester. Anaerobic bio-digesters generally process the organic material by treatment with organisms, which can be obligate or facultative bacteria and/or archaea. These organisms can, using biochemical reactions, convert organic material into a variety of products. Among these products are a mixture of gases, generally referred to as biogas, and a mixture of liquids and solids, generally referred to as biodigestate.

Biogas can include methane, carbon dioxide, and amounts of other gases. Biogas can be burned to provide electricity locally, and can also be transferred to utility companies or transmission networks as natural gas. However, biogas from an anaerobic bio-digester can contain impurities that must be removed before transmission to utility companies. These impurities, which can include carbon dioxide and nitrogen, can be harmful to the environment and are generally disposed of as waste products.

Concerns about overuse of fossil fuels, based in part on environmental concerns and their substantially non-renewable nature, have generated interest in biological sources of energy. Biological energy sources can be desirable because the processes used to produce or extract them are generally less damaging to the environment. Biological energy sources can also be renewable because they are generally derived from plant and/or animal material.

Bio-production facilities can use biological organisms and processes to generate useful products, including biological energy sources, from raw materials. Examples of bio-production facilities include ethanol plants and bio-diesel plants. In bio-production facilities, feedstock is provided to organisms, such as yeasts or algae, which use biochemical processes to generate products that can be useful, such as ethanol or triglycerides, respectively.

One problem common to stand-alone waste conversion facilities and bio-production facilities is that both use products that must be acquired from external sources. These products include feedstock for the bio-production facilities, and organic material for waste conversion facilities. Importing products from external sources can cause loss of efficiency (caused by down-time and need to transport, for example) and can incur significant expenses on the operation of these facilities.

In view of the foregoing, it would be desirable to provide a system that can improve efficiency and performance of waste conversion facilities, bio-production facilities, and other facilities by reducing reliance upon external sources of materials. It would also be desirable to provide a system that reduces the need to dispose of by-products and waste products generated in waste conversion facilities, bio-production facilities, and other facilities.

SUMMARY OF THE DISCLOSURE

Methods and systems for processing organic waste material using an integrated, modular facility are provided. These methods and systems include integrating an anaerobic bio-digester module and nutrient recovery module with a bio-production module, in which the anaerobic bio-digester module can provide feedstock for the bio-production module, and the bio-production module can provide organic material for the anaerobic bio-digester. Methods and systems for integrating an anaerobic bio-digester module with a gas cleaner module are also provided, which can recover nutrients while cleaning the biogas produced by the anaerobic bio-digester module.

For example, a facility for processing organic waste including an anaerobic bio-digester module, a nutrient recovery module, and an enclosed bio-production module can be used. The anaerobic bio-digester module can be configured to digest the organic waste, and the digestion of the organic waste can produce biogas and biodigestate. The nutrient recovery module can be configured to separate a liquid separate from the biodigestate. The enclosed bio-production module can be configured to biologically convert a feedstock to a bio-product, wherein the feedstock includes liquid separate from the nutrient recovery module, and the anaerobic bio-digester module, the nutrient recovery module, and the enclosed bio-production module are modules in an integrated facility.

In some embodiments, the enclosed bio-production module can be a algal incubator module, and the bio-product can include lipids. In some embodiments, the algal incubator module is further configured to produce algal products as a by-product, and the anaerobic bio-digester module is further configured to digest the algal products, wherein the digestion of the algal products can produce biogas and biodigestate.

In some embodiments, the bio-production module can be a bio-diesel production facility and the bio-product can be bio-diesel fatty acids, wherein the bio-diesel production facility includes an algal incubator that can be configured to biologically convert the feedstock into lipids, and a bio-diesel plant, wherein the bio-diesel plant can be configured to convert the lipids into bio-diesel fatty acids. In some embodiments, the bio-diesel plant can be further configured to produce glycerol as a by-product, and the anaerobic bio-digester module can be further configured to digest the glycerol, wherein the digestion of the glycerol can produce biogas and biodigestate.

In some embodiments, the bio-production module can be a fermentation module and the bio-product can be ethanol. In some embodiments, the fermentation module can be further configured to produce thin stillage and wet distiller's grains as by-products, and the anaerobic bio-digester module can be further configured to digest at least one of the thin stillage and wet distiller's grains, wherein the digestion of the thin stillage and wet distiller's grains can produce biogas and biodigestate.

In some embodiments, the integrated, modular facility can include an organic waste generator module, wherein organic waste is produced. In some embodiments, the organic waste generator module is a cattle feedlot module, wherein the cattle feedlot module can be configured to receive feed and produce organic waste in the form of manure. In some embodiments, the organic waste also contains animal offal and carcasses.

In some embodiments, the integrated, modular facility further includes a specified risk material ("SRM") module, wherein the SRM module can be configured to receive animal offal, neutralize at least one pathogen or high-risk material contained within the animal offal, and produce disinfected animal offal, and wherein the organic waste includes the disinfected animal offal.

In some cases, the organic waste contains embedded hard particulates, and the integrated, modular facility can further include a waste processing module, wherein the waste processing module can receive the organic waste, remove the embedded hard particulates, and dilute the organic waste with a diluent. The diluent can include biodigestate. In some embodiments, the waste processing module includes a waste disruptor and a segregator, the waste disruptor can disrupt the organic waste to release at least one of the disrupted hard particulates, and the segregator can segregate the released hard particulates before the organic waste is diluted with a diluent. Examples of such waste processing modules are described in co-pending U.S. patent application titled "Apparatus, Methods And Systems For Handling And Processing waste Material," U.S. patent application Ser. No. 12/004,686, filed on Dec. 21, 2007, and published as US 2009-0159529 A1, which is incorporated herein by reference in its entirety.

In some embodiments, the integrated, modular facility further includes a gas cleaner module, wherein the gas cleaner module can be configured to remove contaminants from the biogas to produce cleaned biogas. In certain embodiments, the gas cleaner module can be configured to recover at least one nutrient from the biogas. The nutrient can be ammonia, for example. The cleaned biogas can be transferred to a natural gas distribution network, such as a natural gas transmission network.

In some embodiments, the integrated, modular facility further includes a co-generator module that can be configured to combust a fuel to produce heat and electricity, wherein the fuel can include, in some embodiments, cleaned biogas. The electricity can be transferred to an electric power transmission network in some embodiments. In some embodiments, at least some of the heat or the electricity can be transferred to the anaerobic bio-digester module, or otherwise used within the integrated facility.

In some embodiments, the integrated, modular facility further includes a control system in communication with at least one of the modules, wherein the control system can be configured to monitor the facility and to adjust operating characteristics of the facility.

Also described is an integrated, modular facility for processing organic waste including an anaerobic bio-digester module, wherein the anaerobic bio-digester module is configured to digest the organic waste, and wherein the digestion of the organic waste can produce biogas, and a gas cleaner module, wherein the gas cleaner module is configured to recover at least one nutrient from the biogas.

In some embodiments, the integrated, modular facility can further include an enclosed bio-production module, wherein the enclosed bio-production module is configured to biologically convert a feedstock to a bio-product and at least one by-product. In certain embodiments, the enclosed bio-production module can include an algal incubator module, and the bio-product can be lipids.

In certain embodiments, the bio-production module is a fermentation module wherein the bio-product can be ethanol.

In some embodiments, the integrated, modular facility can further include a nutrient recovery module, wherein the nutrient recovery module is configured to separate the biodigestate, and the separation of the biodigestate can produce at least a liquid separate and a solid separate.

Additionally, an integrated, modular facility for processing organic waste including an enclosed bio-production module and an anaerobic bio-digester module. In such embodiments, the enclosed bio-production module is configured to biologically convert a feedstock to a bio-product and a by-product. Moreover, the anaerobic bio-digester module is configured to digest the organic waste and the by-product, and wherein the digestion of the organic waste and the by-product can produce biogas and biodigestate is described.

BRIEF DESCRIPTION OF THE DRAWINGS

The above and other advantages of the present invention will become more apparent upon consideration of the following detailed description, taken in conjunction with the accompanying drawings, in which like reference characters refer to like parts throughout, and in which.

DETAILED DESCRIPTION OF THE DISCLOSURE

Methods and systems for processing organic waste are provided and described with reference to FIGS. 1-7.

Figure 1:
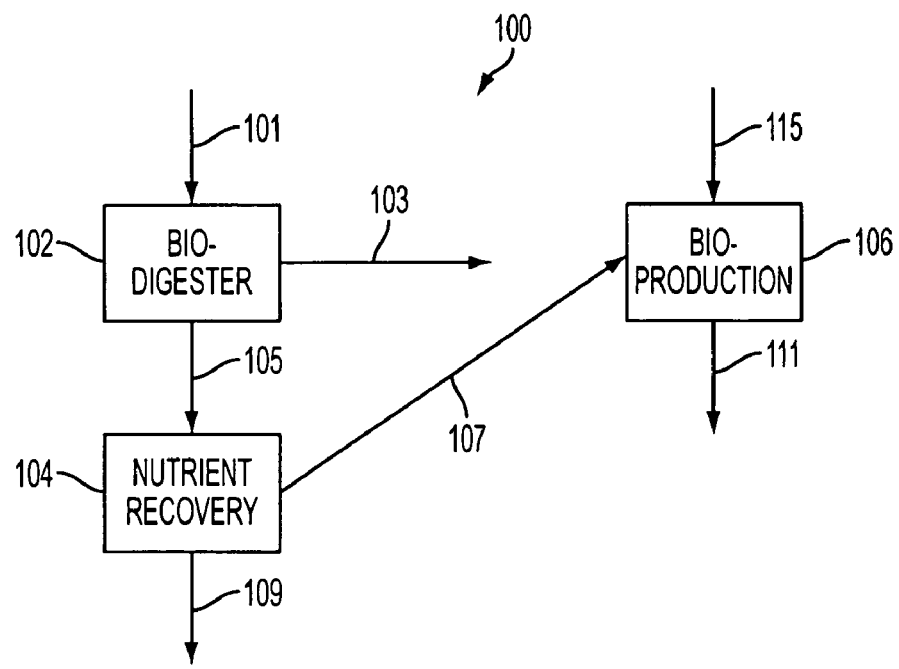
FIG. 1 illustrates a schematic view of an exemplary integrated, modular facility for processing organic waste in accordance with an embodiment of the present invention.

FIG. 1 illustrates a schematic view of exemplary integrated, modular facility 100 for processing organic waste in accordance with an embodiment of the present invention. Integrated, modular facility 100 includes anaerobic bio-digester module 102, nutrient recovery module 104, and bio-production module 106.

An integrated, modular facility in this context means that the individual modules are configured to make use of materials from other modules. Examples of these integrations can include using inputs of certain modules that contain outputs of other modules or vice versa, having common inputs between modules, receiving and/or processing products or by-products of other modules, extracting materials from products of other modules, and removing contaminants from products of other modules. An integrated, modular facility can be advantageous because efficiency can be increased by, for example, reducing reliance upon external resources, permitting customization of products produced by modules to fit system needs (because the destination of the product is known), internalizing processes that otherwise would require external service providers, and permitting shared use of common resources, such as electricity and water, for example. Further advantages can be realized from the reuse of by-products and waste products of individual modules, which would otherwise need to be disposed of, can occur.

Modules can be components of the integrated facility that generally contain systems that process materials. The processing can include digesting, fermenting, separating, disinfecting, combusting, diluting, powering, and heating, for example. The modules can be enclosed and physically distinct from other modules, but interact with other modules within the integrated facility, and can, in some embodiments, be merged with or share components with other modules. For example, modules can have common supplies of electricity, heat, water, and/or materials used in processing, and can be enclosed in the same building or physical enclosure.

Integration of the modules in a facility of the present invention can be enhanced in some embodiments by having the individual modules be in proximity to each other, but this is not required. Also, the integration of modules can be accomplished by having modules in proximity. For example, modules can be in the same locality, or spatially close enough to share equipment, staff, a utility system (e.g., electric power, water service), or a control system. Proximity provides further advantages, as idle time of individual modules can be reduced, and expense related to storage and transportation of products and by-products of individual modules can be reduced. Proximity may also provide advantages in that it allows customization of products, such as feedstock, for example, to fit the requirements of individual modules.

Integration can be also be accomplished by direct connection between individual modules, such as by transporting module outputs by pipes. Direct connection can provide similar benefits to proximity in that idle time and the storage and transportation costs related to materials used by the modules can be reduced.

Integration of the modular facility can also be enhanced or accomplished by a control and monitoring system that can allow monitoring of the modules, as well as control of the operational parameters of the modules. The control and monitoring system can be used to monitor at least one operational parameter of at least one individual module of the facility. Additionally, the control and monitoring system can be used to monitor operational parameters of the facility as an entirety. These parameters can include, for example, performance, flow rate, inputs, outputs, module status, alarms, temperature, power consumption, material content. The control and monitoring system can also be used to control or adjust operational parameters of the individual modules of the facility as an entirety. Having a control system for the modular facility provides advantages in the form of increased efficiency and responsiveness to the needs of users. Increased efficiency can arise, for example, in the form of increased responsiveness to material availability, increased responsiveness to market demand for products, increased responsiveness to alarms or changes in module status, greater awareness of facility operation, and decreased downtime due to greater awareness of facility operation.

One embodiment of the control and monitoring system can be a computer system, having, for example, at least one processor, sensors and controllers in communication with individual modules, at least one display, and at least one input device. The computer system can use the sensors to monitor and present a user with the status of operational parameters of the system. The user can use the input device to cause the computer system to adjust the parameters to suit the user's needs. The computer system, in some embodiments, can also automatically or algorithmically adjust the parameters to meet desired benchmarks or performance levels without user intervention.

Organic waste 101 can be, and generally is, a mixture of discarded organic material having relatively low commercial value. Organic waste 101 can contain any suitable material that includes organic and organically-derived material. For example, organic waste 101 can include by-products from various industries, including agriculture, food processing, animal and plant processing, and livestock. Examples of organic waste 101 include, but are not limited to: livestock manure, animal carcasses and offal, plant material, wastewater, sewage, food processing, and any combination thereof. Organic waste 101 can also include human-derived waste, such as sewage and wastewater, discarded food, plant, or animal matter, and the like.

Organic waste 101 can be provided by any suitable source, including those described above. In some embodiments, the organic waste source is proximate to system 100, like a nearby feedlot or meat processing plant, for example. Such proximity can allow efficient and rapid processing of organic waste 101.

In some embodiments, organic waste 101 can be provided from a location or source more distant from system 100. This positioning may be more suitable in cases where system 100 is located in a central location to process organic waste from multiple sources situated in the local neighborhood or region.

Anaerobic bio-digester module 102 can reduce the environmental impact of organic waste 101 and can be used in conversion or extraction of useful products from organic waste 101. Anaerobic bio-digester module 102 can include an enclosed container, which can be a vat or vessel or housing, where anaerobic bio-digestion of organic waste 101 takes place. Anaerobic bio-digester module 102 is enclosed generally to prevent exposure to air, or other atmospheric or local contaminants. Many anaerobic bio-digestion facilities and systems are known (e.g., horizontal or plug-flow, multiple-tank, vertical tank, complete mix, and covered lagoon digesters) and any of these can be suitable for purposes of the present invention.

The anaerobic bio-digestion of organic waste 101 is performed by organisms, which can, as described hereinabove, produce biogas 103 and biodigestate 105. Biogas 103 generally contains a mixture of gaseous methane, carbon dioxide, and nitrogen (which can be in the form of ammonia), but may also contain quantities of hydrogen, sulfides, siloxanes, oxygen, and airborne particulates. Biogas 103 can rise within the enclosed container containing the organisms, and can accumulate in the headspace of the enclosed container. Biogas 103 can be removed from anaerobic bio-digester module 102, either continuously or in batch, so more biogas 103 can be allowed to accumulate in the enclosed container.

In addition to biogas 103, biodigestate 105 can be produced as a result of the anaerobic bio-digestion of organic material 101. Biodigestate 105 can be a mixture of a variety of materials, and can include organic material not digested by the organisms, by-products of anaerobic bio-digestion released by the organisms, and in some embodiments, the organisms themselves. These biodigestate components can be in either liquid or solid form, and can be present in any suitable amount. The amount of each component within biodigestate 105 can, in some embodiments, be adjusted. For example, the amount of time the organisms are exposed to organic material 101 can be varied to alter the amounts of undigested organic material and anaerobic bio-digestion by-products.

Anaerobic bio-digester module 102 can operate continuously or it can batch-process organic waste 101. Biogas 103 and biodigestate 105 can be further processed, as shown below, to produce useful products. Even without subsequent processing, however, biogas 103 and biodigestate 105 can be useful (e.g., as fuel and a fertilizer compound respectively).

Biodigestate 105, when it is removed from anaerobic biodigester module 102, may include potentially useful materials and chemicals. To recover or isolate such material or chemicals, further processing of biodigestate 105 may be needed. Biodigestate separation and processing can be performed within nutrient recovery module 104. Nutrient recovery module 104 can include systems (e.g., machines or devices) that perform nutrient recovery, which are interconnected and/or interrelated such that they can process the biodigestate serially or in parallel. Examples of such systems include centrifuges, precipitation reactors, and settling tanks.

Nutrient recovery can be done continuously or in batch processes. Nutrient recovery generally involves extracting materials from biodigestate 105 based upon differing properties of the materials. Examples of these material properties include chemical properties (e.g, acidity), density, and size. Recovery can be performed serially or in parallel processes.

Biodigestate 105 can be separated within nutrient recovery module 104 based upon matter state, which can create at least two separates, one having a greater liquid content than the other. This can be done by any known method of separating a liquid from a solid or slurry, including using a centrifuge, settling, or rotating and shaking screens, for example. Liquid separate 107 can be a separate having relatively greater liquid content, and can be separated from biodigestate 105 within nutrient recovery module 104. Liquid separate 107 can include soluble nitrogen, phosphorous, and water, and in some embodiments nutrients may be precipitated from the liquid separate for use as fertilizer, for example.

Subsequent processing, which can be mechanical or chemical, can also be done on liquid separate 107 to enhance its nutrient content. Exemplary processes to enhance the nutrient content include lime precipitation, ammonia stripping, and pH adjustment. An exemplary way of separating biodigestate 105 to produce liquid separate 107 is described in U.S. Pat. No. 7,014,768 which is herein incorporated by reference.

Solid separate 109 can also be separated from biodigestate 105 within nutrient recovery module 104. Solid separate 109 can have relatively greater solid content compared to liquid separate 107. Solid separate may be used as compost or as a soil substitute. Solid separate 109 can also be formed into pellets or bales to facilitate transport, or may be useful in such form, and can be used as fungal feedstock. Solid separate 109 can also be enriched with nutrients, such as nitrates and ammonia, by any known method for use as a fertilizer in some embodiments.

Enclosed bio-production module 106 can be an enclosed system that can produce bio-product 111. Enclosed bio-production module 106 can include an enclosed container wherein organisms biologically convert a feedstock into a bio-product. Bio-product 111 can be any product of a biological or organic or biochemical process whereby one or more materials is biologically converted into one or more products. Bio-products can have general utility for industrial or commercial processes. Bio-products can also be advantageous because, for example, they can be used as substitutes for materials that are more expensive and/or more damaging to the environment. Bio-product 111 can be advantageous because it can be produced in a bio-production module less expensively, with less environmental impact, or using renewable feedstock. For example, bio-product 111 can be ethanol (e.g., produced from the fermentation of sugars), lipids (e.g., synthesized by organisms), or bio-diesel fatty acids. Bio-product 111 can be harvested through any known method or process, and remnant materials, or by-products, can remain.

As discussed below, by-products can also be produced in the process of producing bio-product 111. These by-products can have useful applications as well. Please see the discussion of bio-production module 206 below for additional details regarding bio-production module 106.

Biological conversion in this context means receive a feedstock input and through biological or biochemical processing produce at least one bio-product that has a different form from the input. Biological conversion can comprise digestion (both aerobic and anaerobic), metabolic processes, esterification, fermentation, heterotrophic processes, photosynthetic processes, anabolic processes and catabolic processes, for example. In some embodiments, the biological conversion can be done by organisms. Examples of organisms that can biologically convert feedstock 115 into bio-product 111 include algae, yeast, and bacteria. In one example, biological conversion can comprise yeast catabolically processing sugar and secreting ethanol as a bioproduct. In another example, biological conversion can comprise algae anabolically producing lipids from nutrients.

Feedstock 115 can be a raw material that undergoes biological conversion, and as shown in system 100, includes liquid separate 107. Examples of feedstock include sugars, nutrients, lipids, and grain. Liquid separate 107 can function as feed for the organisms in some embodiments. Liquid separate 107 functions in some embodiments as a supplement, to provide nutrients used in biological conversion processes.

In system 100, feedstock 115 includes at least a portion of liquid separate 107 separated from biodigestate 105. In some embodiments, feedstock 115 can include non-separated biodigestate produced by digester 102. System 100 can be advantageous because externally-acquired feedstock can be expensive, and require storage space and transportation expense. Storage of feedstock under prior art methods can also be problematic because some types of feedstock, such as fertilizer in the form of animal manure or grain containing sugars, can decay over time. Furthermore, using liquid separate 107 onsite in system 100 can reduce or eliminate the expense involved with storing or transporting liquid separate 107. Liquid separate 107 can also advantageously be further processed to improve its feedstock qualities under the present invention, such as by nutrient addition or supplementation.

Figure 2:
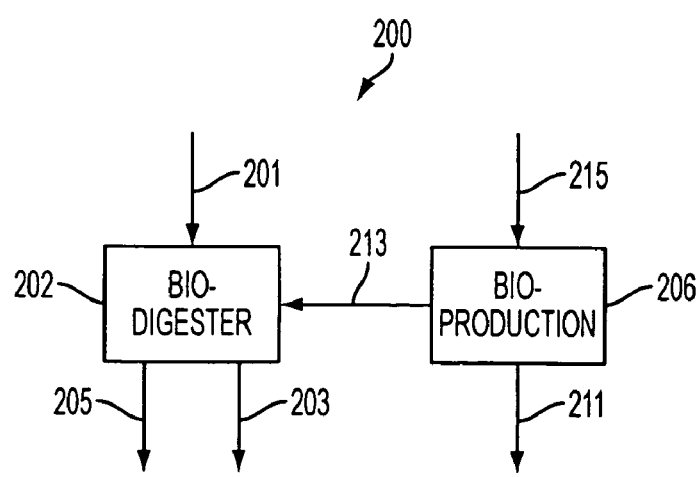
FIG. 2 illustrates a schematic view of an exemplary integrated, modular facility for processing organic waste in accordance with an embodiment of the present invention.

FIG. 2 illustrates a schematic view of an exemplary integrated, modular facility for processing organic waste in accordance with an embodiment of the present invention. Integrated, modular facility 200 includes enclosed bio-production module 206 and anaerobic bio-digester module 202.

Enclosed bio-production module 206, which is similar to bio-production module 106, contains organisms housed therein, which biologically convert feedstock 215 as described above to produce bio-product 211 and by-product 213. Feedstock 215 can comprise a liquid separate separated from biodigestate 205 (as described in system 100), but this is optional. Examples of organisms within bio-production module 206 include algae, yeast, and bacteria.

By-product 213 can include any organic product that is also produced when the bio-production module 206 biologically converts feedstock 215 into bio-product 211. By-product 213 generally has relatively lower commercial value than bio-product 211. By-product 213, in previously known systems, generally must be disposed of, and can be a source of transport and storage costs. In some cases (e.g., wet distiller's grains produced when grain is fermented), by-products need further processing for preservation purposes, further incurring expense.

An exemplary embodiment of bio-production module 206 can be a fermentation module, which has feedstock 215 that includes grain. In some embodiments, as described above, feedstock 215 can include liquid separate from a nutrient recovery module. Feedstock 215 can be catabolically processed by yeast contained within the fermentation module, and secrete ethanol as bio-product 211. By-product 213, which remains after the ethanol is removed, can include thin stillage and wet distiller's grains, either alone or in combination with one another.

Another exemplary embodiment of bio-production module 206 is an algal incubator, containing algae that can consume feedstock 215, which can include a nutrient solution. As noted above in reference to bio-production module 106, the nutrient solution also includes liquid separate. The algae can anabolically process the feedstock and produce lipids or triglycerides as bio-product 211. The algae can be subsequently harvested, and lipids or triglycerides 211 can be removed by subsequent processing (e.g., using enzymes), thereby leaving algal material as by-product 213.

Another exemplary embodiment of bio-production module 206 can be a bio-diesel production module, which can include an algal incubator and a bio-diesel plant. The algal incubator and the bio-diesel plant can be can be contained in the same building or enclosure, or can be enclosed separately. The bio-diesel production module can contain algae, which as described above can produce lipids or triglycerides from a feedstock. As noted above in reference to bio-production module 106, the feedstock can include liquid separate. The lipids can be converted into bio-product 211, in this case bio-diesel fatty acids, within bio-production module 206 by any known method (e.g., chemically via transesterification or hydrolysis). Other methods of converting lipids into bio-diesel that can be used by the bio-diesel plant include base catalyst transesterification, directed acid catalyzed esterification, and conversion using acid catalysis. Glycerol, which can be a by-product of converting lipids into bio-diesel, can sink to the bottom of the container within the bio-diesel plant and be removed from bio-diesel module 206 as by-product 213.

Anaerobic bio-digester module 202 generally may be similar to anaerobic bio-digester module 102 from FIG. 1, as described hereinabove. In addition to digesting organic waste 201, however, anaerobic bio-digester module 202 can digest at least a portion of by-product 213, since by-product 213 includes organic material, to produce biogas 203 and biodigestate 205.

In prior art systems, by-product 213 generally needed to be stored and transported because by-product 213 was generally no longer use to enclosed bio-production module 206. The present invention can be advantageous because it can make productive use of by-product 213 within integrated, modular facility 200, without incurring excess cost for storage and transport. Furthermore, greater efficiency can be realized by the present invention because additional organic material can be provided to anaerobic bio-digester module 202, reducing the need to import external organic material for digestion.

Figure 3:
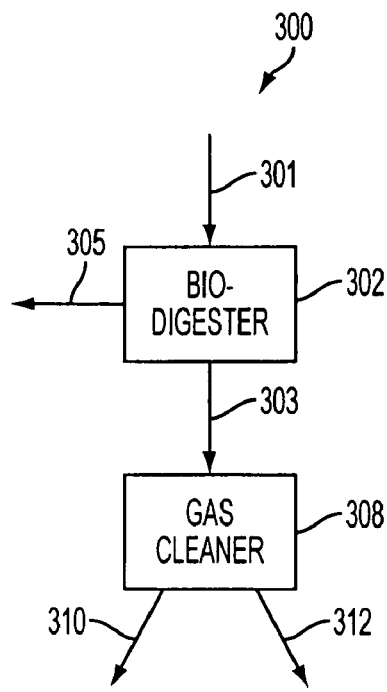
FIG. 3 illustrates a schematic view of an exemplary integrated, modular facility for processing organic waste in accordance with an embodiment of the present invention.

FIG. 3 illustrates a schematic view of an exemplary system for processing organic waste in accordance with an embodiment of the present invention. System 300 includes anaerobic bio-digester module 302 and gas cleaner module 308.

Integrated, modular facility 300 can be advantageous because it can recover nutrients, which can be useful products. The by-products of biogas cleaning, if disposed of as waste, can contribute to the greenhouse effect and pollute the air, among other problems. Integrated, modular facility 300 can also remove contaminants, which otherwise might need to be performed by external sources and entail additional costs. By integrating anaerobic bio-digester 302 with gas cleaner 308, improved efficiency can be realized, because biogas storage and transfer costs can be eliminated.

Anaerobic bio-digester module 302 generally may be similar to anaerobic bio-digester module 102 from FIG. 1, as described hereinabove, and can digest organic waste 301 to produce biogas 303 and biodigestate 305.

It is often desirable to remove contaminants from biogas 303. Contaminants generally can be any material in biogas 303 other than methane, including carbon dioxide, nitrogen, ammonia, sulfides, and siloxanes. Biogas 303 generally does not meet standards for introduction into a natural gas utility network, but after contaminants are removed, can meet those standards. Also, contaminants in biogas 303 can make it undesirable, although possible, to combust before contaminants are removed. Combusting biogas 303 prior to performing any processing on biogas 303 can result in damage to the environment, through release of gases that can be toxic or noxious, such as sulfides and nitrogen oxides, and by release of greenhouse gases such as carbon dioxide. The presence of contaminants in combusted biogas can also result in poorer combustion characteristics. In prior art systems, biogas 303 can be cleaned, but the by-products of the cleaning generally can no longer be used, and generally are stored and transported as waste.

Integrated, modular facility 300 can be advantageous because nutrients 310 can be recovered within gas cleaner module 308. Nutrients 310 can have utility as fertilizer, for example, and can reduce the amount of contaminants that need to be disposed of as waste. Nutrients 310 include substances that have nutritional value to organisms, and examples include ammonia, ammonium compounds, and nitrates. In some embodiments, gas cleaner 308 recovers ammonia from biogas 303. This can be done, for example, by precipitating ammonia from the biogas. In certain embodiments, biogas 303 can be exposed to an acid, which can be adsorbed on a solid substrate (e.g., solid separate 305, wood chips, or straw). The ammonia can then react with the acid and produce non-volatile ammonium compounds. The ammonium compounds can then be used in useful products (e.g., fertilizer), with or without additional processing.

To recover nutrients 310, gas cleaner module 308 can utilize any known method of separating materials from biogas 303. The separation can be performed on basis of physical properties (e.g., density, and condensation point) or on the basis of chemical properties (e.g., pH, solubility, and reactivity), and can be done continuously or by batch processing. In some embodiments, nutrients 310 can be removed from biogas 303 by contacting biogas 303 with an acid within a container. Multiple separation methods can be used, and they can be applied sequentially or in parallel with each other.

Any known method treating or scrubbing a gas to recover a material within the gas can be used to separate contaminants from biogas 303. In certain embodiments, biogas 303 is cooled, and contaminants are condensed and removed from gas cleaner module 308.

After separation Has occurred, cleaned biogas 312 can be removed from gas cleaner module 308, leaving material that includes nutrients 310 within gas cleaner module 308. Cleaned biogas 312 can be a gas mixture containing methane that has fewer contaminants than present in biogas 303. Cleaned biogas 312 can be sold or transferred to a natural gas transmission network in some embodiments. Cleaned biogas 312 in certain embodiments can be combusted locally (e.g., in a co-generator). Please see FIG. 7 and the accompanying text for greater detail regarding the uses of cleaned biogas 312.

Figure 4:
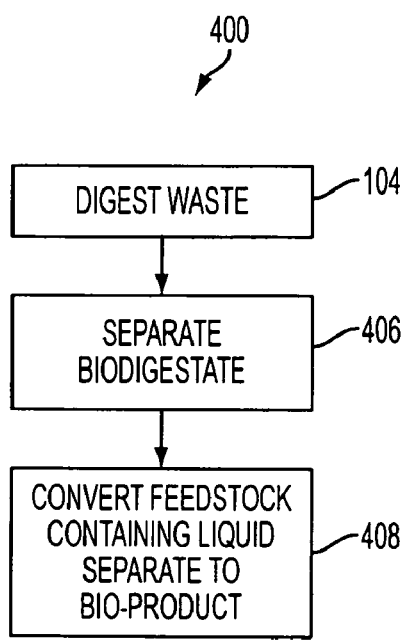
FIG. 4 is a flow chart illustrating an exemplary process for processing organic waste in accordance with an embodiment of the present invention.

FIG. 4 is a flow chart illustrating an exemplary process for processing organic waste using an integrated, modular facility in accordance with an embodiment of the present invention.

At step 404, the organic waste is digested by an anaerobic bio-digester module, which is configured to digest the organic waste and can produce biogas and biodigestate, as described herein.

At step 405, the biodigestate is separated by a nutrient recovery module, producing a liquid separate, as described herein.

At step 408, a feedstock, comprising the liquid separate from the nutrient recovery module, is biologically converted into a bio-product in an enclosed bio-production module. This can be done, by organisms within an enclosed bio-production module, as described herein.

Process 400 can be advantageous for similar reasons as integrated, modular facility 100. These reasons include avoiding the need for externally produced feedstock, avoiding expense entailed in storage and transportation, and these problems can be avoided or reduced using the present invention. Storage of feedstock under prior art methods can also be problematic because some types of feedstock, such as fertilizer in the form of animal manure or grain containing sugars, can decay over time. Furthermore, the liquid separate can be used as it is produced by process 400, which can reduce or eliminate the expense involved with storing or transporting the liquid separate.

Figure 5:
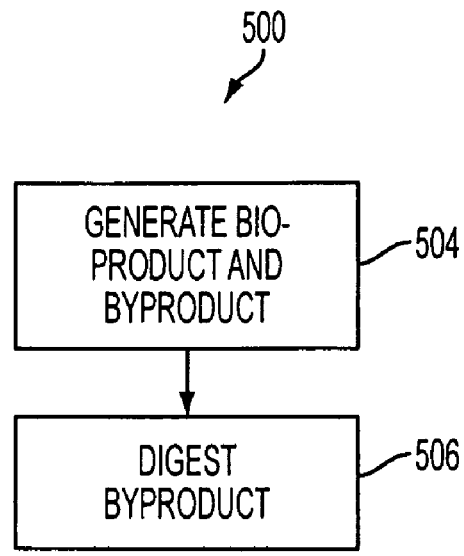
FIG. 5 is a flow chart illustrating an exemplary process for processing organic waste in accordance with an embodiment of the present invention.

FIG. 5 is a flow chart illustrating an exemplary process for processing organic waste using an integrated, modular facility in accordance with an embodiment of the present invention. The enclosed bio-production module can function as any suitable enclosed bio-production module described above. As discussed above, the feedstock can comprise liquid separate separated from biodigestate from an anaerobic bio-digester.

At step 504, the enclosed bio-production module biologically converts a feedstock into a bio-product and a by-product, which can function similarly as described herein.

At step 506, the by-product is digested in an anaerobic bio-digester module to produce biogas and biodigestate. Process 500 can be advantageous, as discussed above, because it can use by-products from the enclosed bio-production module, which could otherwise require disposal or costly storage or transport, in the same integrated, modular facility.

Figure 6:
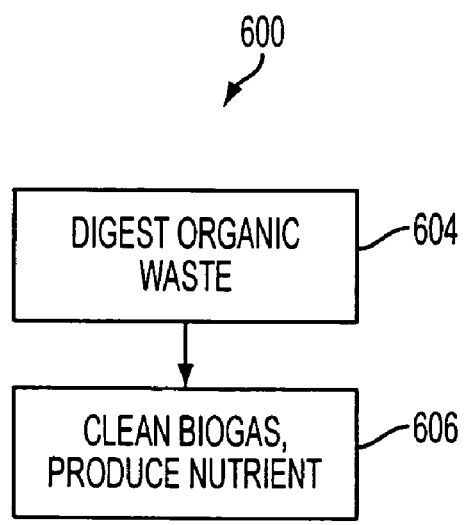
FIG. 6 is a flow chart illustrating an exemplary process for processing organic waste in accordance with an embodiment of the present invention.

FIG. 6 is a flow chart illustrating an exemplary process for processing organic waste using an integrated, modular facility in accordance with an embodiment of the present invention.

At step 604, the organic waste is digested by an anaerobic bio-digester module, as described herein, which can produce biogas.

At step 606, the biogas is cleaned using a gas cleaner module, and a nutrient is recovered from the biogas. In some embodiments, ammonia is recovered from the biogas. This can be done by passing the biogas through a substrate with acid adsorbed thereon, wherein the acid can react with the ammonia and form non-volatile ammonium compounds. This can also be done by any known method of scrubbing a gas to remove ammonia. Other nitrogen-based or other compounds can also be recovered from the biogas in other embodiments.

Process 600 can be advantageous, as discussed above, because it can recover nutrients, which can be useful, instead of releasing by-products from biogas cleaning into the environment, where they may contribute to the greenhouse effect and pollute the air, among other problems. Improved efficiency can also be realized, because biogas storage and transfer costs can be eliminated as a result of integrating the anaerobic bio-digester from step 604 with the biogas cleaner from step 606.

Figure 7:
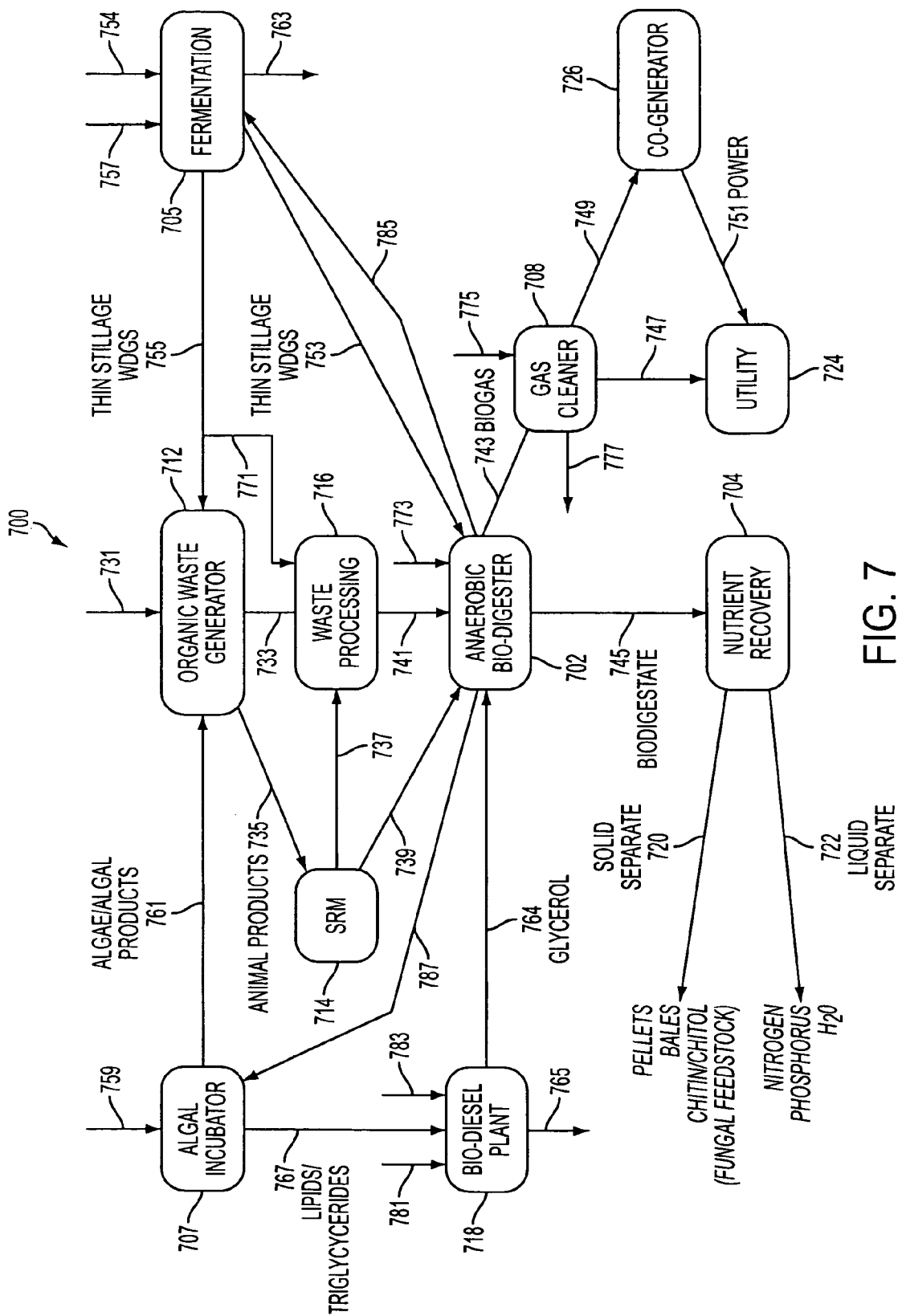
FIG. 7 illustrates a schematic view of an exemplary integrated, modular facility for processing organic waste in accordance with an embodiment of the present invention.

FIG. 7 illustrates a schematic view of an exemplary integrated, modular system for processing organic waste in accordance with an embodiment of the present invention. System 700 comprises organic waste generator module 712, specified risk material module ("SRM" module) 714, waste handler module 716, anaerobic bio-digester module 702, nutrient recovery module 704, gas cleaner module 708, co-generator module 726, fermentation module 705, algal incubator module 707, and bio-diesel plane module 718.

Organic waste generator module 712 is a source of organic waste, and is similar to the organic waste sources described hereinabove. Organic waste generator module 712 can be any source of organic waste, including, for example, livestock feedlots, municipal waste plants, and meat processing plants. Organic waste can be provided, for example, in the forms of livestock manure, sewage, or animal rendering (e.g., carcasses). For purposes of enhanced integration, as discussed above, organic waste generator module 712 can be proximal to other modules, but is not required to do so. In some embodiments, organic waste generator module 712 can be a cattle feedlot, where cattle consume feed and produce organic waste. Feed can include any suitable nutrient-containing material, and can include wet distiller's grains and thin stillage 755, and algal products 761. Water and silage (not shown in figure) can also be consumed within organic waste generator module 712. Organic waste 733 and animal rendering 735 can be produced within organic waste generator module 712.

As noted above, organic waste can include animal tissue and offal. This tissue and offal can include animal heads, brains, eyes, spinal cords, and other organs, for example. Certain types of animal offal, such as cattle offal, can contain pathogens. Examples of pathogens in organic waste can include pathogens causing bovine spongiform encephalopathy, and avian flu viruses. For this reason, cattle rendering, for example, can be denoted as "specified risk material" ("SRM"). It can desirable to disinfect the SRM, for example, to reduce the risk of disease transmission to humans or livestock that can be exposed to organic waste. SRM module 714 is an optional aspect of system 700, and can be used in embodiments where it is desirable to disinfect animal rendering.

SRM module 714 can be used to neutralize or disinfect organic waste containing SRM 735, by neutralizing at least a portion of the pathogens contained therein (e.g., by using heat, or by using chemicals). SRM module 714 in some embodiments can be a high-temperature oven unit, which heats organic waste containing SRM 735 from the aforementioned sources of organic waste until they reach a temperature generally higher than what the pathogens can survive.

Waste handler module 716 is an optional aspect of 700, and can be used in embodiments where the organic waste is heterogeneous, and may contain hard particulates. The hard particulates can comprise rocks, metal, wood, bone, and plastic contaminants, and can inhibit processing of the organic waste because they can not be amenable to processes such as anaerobic bio-digestion. Hard particulates can also potentially cause damage to machinery used in subsequent processing, such as machinery used in nutrient recovery module 704 or anaerobic bio-digester 702, for example. Waste handler module 716 can remove hard particulates from organic waste 733 from organic waste generator 712 and/or organic waste 737 from SRM unit 714, either alone or in combination.

Waste handler module 716 can additionally dilute the organic waste using liquid diluent 771 to produce processed organic waste 741.

Waste handler 716 may accomplish this in some embodiments by disrupting the organic waste, removing hard particulates and diluting the organic waste using liquid diluent 771 to produce processed organic waste 741. These exemplary processes are each optional, and can be done in any combination or order. In some embodiments, diluent 771 can include biodigestate 745.

Anaerobic bio-digester 702 generally may be similar to anaerobic bio-digester module 102 from FIG. 1, as described hereinabove. Anaerobic bio-digester, in addition to organic waste, can digest cosubstrates 773, which can include glycerol 764 (which can be provided by bio-diesel plant 718), thin stillage and wet distiller's grains 753 (which can be provided by fermentation unit 705), and algal products 761 (which can be provided by algal incubator 707), to produce biogas 743 and biodigestate 745.

Nutrient recovery module 704 generally may be similar to nutrient recovery module 104 from FIG. 1, as described hereinabove. Within nutrient recovery module 704, nutrients can generally be recovered from biodigestate 745. Also, solid separate 720 and liquid separate 722 can be separated from biodigestate 745 within nutrient recovery module 704.

Gas cleaner module 708 can function similarly to gas cleaner module 308 described above. Gas cleaner module 708 can clean biogas 743 to recover nutrients 777. In some embodiments, solid separate 720 can have acid adsorbed thereon, and can be used to recover ammonia from biogas 743. Further processing can be performed in some embodiments to remove other contaminants from biogas 743 in gas cleaner module 708. For some example, in some embodiments biogas 743 can be cryogenically cooled so contaminants can be separated and removed from biogas 743. Cleaned biogas 747 can then be transferred to optional transmission network 724. Transmission network 724 can be any commercial or private transmission network used for production of energy, such as a natural gas transmission network or an electrical power transmission network, for example.

Co-generator module 726 is an optional element of system 700. Co-generator module 726 generally burns a fuel (e.g., natural gas) to produce heat and electricity 751, which can be used elsewhere in the system (e.g., electricity can be used to power a pump transporting biodigestate 745 from anaerobic bio-digester module 702 to nutrient recovery module 704, heat and electricity 751 can be used in the fermentation process within fermentation module 705, etc.). In some embodiments, electricity and heat 751 can be transferred to transmission network 724, which can be an electrical power transmission network, for example. The fuel can include biogas 743 from anaerobic bio-digester module 702, and can also include cleaned biogas 749 from gas cleaner module 708. Co-generator output 751 may also include exhaust gases, including carbon dioxide.

Fermentation module 705 is a bio-production module, and functions similarly to the fermentation module embodiment described above with respect to bio-production facilities 106 and 206. Fermentation module 705 can biologically convert feedstock 757 into ethanol 763, and optionally thin stillage and wet distiller's grains 755 and 753. Additionally, fermentation module 705 can receive electricity and heat 779, which can include electricity and heat 751 from co-generator 726, to power any machinery used in fermentation module 705. Water can also be used to produce ethanol in fermentation module 705. Fermentation module 705 may also receive biodigestate or separates thereof, such as biodigestate 785 from anaerobic digester 702, or biodigestate separate from nutrient recovery module 704. Providing such biodigestates or derivatives may advantageously provide readily available and inexpensive nutrient supplements, as well as water, to the fermentation process.

Algal incubator 707 can be a bio-production module, and can function similarly to the algal incubator embodiment described above with respect to bio-production facilities 106 and 206. Within algal incubator 707, feedstock 759, which can include liquid separate 722, can be biologically converted into lipids 767. Algal incubator 707 may also receive biodigestate or separates thereof, such as biodigestate 787 from anaerobic digester 702, or biodigestate separate from nutrient recovery module 704. Providing such biodigestates or derivatives may advantageously provide readily available and inexpensive nutrient supplements, as well as water, to the algal incubation process.

Bio-diesel plant 718 can be part of a bio-diesel production module, as described hereinabove, and can be an enclosed facility or system whereby lipids, which can include lipids 767, can be converted into bio-diesel 765 using any known method of conversion, as described hereinabove. For example, lipids can be chemically converted via transesterification into bio-diesel 765. Bio-diesel plant 718 can also produce glycerol 764 as a by-product of converting lipids into bio-diesel 767. Glycerol 764 produced by bio-diesel plant 718 can be supplied to anaerobic bio-digester 702 as a cosubstrate for digestion. Together, algal incubator 707 and bio-diesel plant 718 can be a bio-production facility in some embodiments, with a bio-product comprising bio-diesel 765, and a by-product comprising glycerol 764.

In some embodiments, alcohol 781 is used by bio-diesel plant 718 to produce bio-diesel 765. Alcohol 781 can include ethanol 763 from fermentation facility 705 in some embodiments. Furthermore, in some embodiments catalyst 783 can be used to produce bio-diesel 765. Catalyst 783 in some embodiments includes a compound that is a base (e.g., sodium hydroxide).

Integrated, modular facility 700 can be advantageous because it can reduce transportation and storage costs of the various products used by each component of the system, which can increase efficiency. Also, because organic material tends to decay over time, integrated, modular facility 700 can obtain greater yield of useful products because reduction of idle time. Although not all possible integrations of integrated, modular facility may be discussed, the outputs of any individual module can be used as inputs for another module and vice versa.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. An integrated, modular facility for processing organic waste, the facility comprising:
   (1) an anaerobic bio-digester module, wherein the anaerobic bio-digester module is configured to digest the organic waste, wherein the digestion of the organic waste produces biogas and biodigestate;
   (2) a nutrient recovery module, wherein the nutrient recovery module is configured to separate a liquid separate from the biodigestate; and
   (3) an enclosed bio-production module, wherein the enclosed bio-production module is configured to biologically convert a feedstock to a bio-product, wherein the feedstock comprises liquid separate from the nutrient recovery module; and,
wherein the enclosed bio-production module comprises an algal incubator module, and wherein the bio-product comprises lipids.

2. The facility of claim 1, wherein the algal incubator module is further configured to produce algal products as a by-product, and the anaerobic biodigester module is further configured to digest the algal products, wherein the digestion of the algal products produces biogas and biodigestate.

3. The facility of claim 1, further comprising an organic waste generator module, wherein organic waste is produced.

4. The facility of claim 3, wherein the organic waste generator module comprises a cattle feedlot module, wherein the cattle feedlot module is configured to receive a feed and produces organic waste comprising manure.

5. The facility of claim 3, wherein the organic waste comprises animal offal.

6. The facility of claim 1, further comprising a gas cleaner module, wherein the gas cleaner module is configured to remove contaminants from the biogas to produce cleaned biogas.

7. The facility of claim 1, further comprising a control system in communication with all of the modules, wherein the control system is configured to monitor the facility and to adjust operating characteristics of the facility.

8. An integrated, modular facility for processing organic waste, the facility comprising:
(1) an anaerobic bio-digester module, wherein the anaerobic bio-digester module is configured to digest the organic waste, wherein the digestion of the organic waste produces biogas and biodigestate;
(2) a nutrient recovery module, wherein the nutrient recovery module is configured to separate a liquid separate from the biodigestate; and
(3) an enclosed bio-production module, wherein the enclosed bio-production module is configured to biologically convert a feedstock to a bio-product, wherein the feedstock comprises liquid separate from the nutrient recovery module; and,
wherein the bio-production module is a bio-diesel production facility and the bio-product comprises bio-diesel fatty acids, and wherein the bio-diesel production facility comprises:
(a) an algal incubator configured to biologically convert the feedstock into lipids; and
(b) a bio-diesel plant, wherein the biodiesel plant is configured to convert the lipids into bio-diesel fatty acids.

9. The facility of claim 8, wherein the bio-diesel plant is further configured to produce glycerol as a by-product, and the anaerobic biodigester module is further configured to digest the glycerol, wherein the digestion of the glycerol produces biogas and biodigestate.

10. The facility of claim 8, further comprising an organic waste generator module, wherein organic waste is produced.

11. The facility of claim 10, wherein the cattle feedlot module is configured to receive a feed and produces organic waste comprising manure.

12. The facility of claim 10, wherein the organic waste comprises animal offal.

13. The facility of claim 8, further comprising a gas cleaner module, wherein the gas cleaner module is configured to remove contaminants from the biogas to produce cleaned biogas.

14. The facility of claim 8, further comprising a control system in communication with all of the modules, wherein the control system is configured to monitor the facility and to adjust operating characteristics of the facility.

15. An integrated, modular facility for processing organic waste, the facility comprising:
(1) an anaerobic bio-digester module, wherein the anaerobic bio-digester module is configured to digest the organic waste, wherein the digestion of the organic waste produces biogas and biodigestate;
(2) a nutrient recovery module, wherein the nutrient recovery module is configured to separate a liquid separate from the biodigestate; and
(3) an enclosed bio-production module, wherein the enclosed bio-production module is configured to biologically convert a feedstock to a bio-product, wherein the feedstock comprises liquid separate from the nutrient recovery module; and, wherein the bio-production module is a fermentation module and wherein the bio-product comprises ethanol.

16. The facility of claim 15, wherein the fermentation module is further configured to produce thin stillage and wet distiller's grains as byproducts, and the anaerobic bio-digester module is further configured to digest at least one of the thin stillage and wet distiller's grains, wherein the digestion of the thin stillage and wet distiller's grains produces biogas and biodigestate.

17. The facility of claim 15, further comprising a gas cleaner module, wherein the gas cleaner module is configured to remove contaminants from the biogas to produce cleaned biogas, and wherein the gas cleaner module is configured to recover at least one nutrient from the biogas.

18. The facility of claim 15, further comprising a gas cleaner module, wherein the gas cleaner module is configured to remove contaminants from the biogas to produce cleaned biogas, wherein the gas cleaner module is configured to recover at least one nutrient from the biogas, and wherein the at least one nutrient comprises ammonia.

19. The facility of claim 15, further comprising a gas cleaner module, wherein the gas cleaner module is configured to remove contaminants from the biogas to produce cleaned biogas, and wherein the cleaned biogas is transferred to a natural gas transmission network.

20. The facility of claim 15, further comprising
(1) a gas cleaner module, wherein the gas cleaner module is configured to remove contaminants from the biogas to produce cleaned biogas; and
(2) a co-generator module, wherein the cogenerator module is configured to combust a fuel to produce heat and electricity, wherein the fuel comprises cleaned biogas.

21. The facility of claim 20, wherein the fuel comprises biogas.

22. The facility of claim 20, wherein the electricity is transferred to an electric power transmission network.

23. The facility of claim 20, wherein at least one of the heat and the electricity are transferred to the anaerobic bio-digester module.

24. The facility of claim 15, further comprising an organic waste generator module, wherein organic waste is produced.

25. The facility of claim 24, wherein the cattle feedlot module is configured to receive a feed and produces organic waste comprising manure.

26. The facility of claim 24, wherein the organic waste comprises animal offal.

27. The facility of claim 15, further comprising a gas cleaner module, wherein the gas cleaner module is configured to remove contaminants from the biogas to produce cleaned biogas.

28. The facility of claim 15, further comprising a control system in communication with all of the modules, wherein the control system is configured to monitor the facility and to adjust operating characteristics of the facility.

29. An integrated, modular facility for processing organic waste, the facility comprising:
 (1) an anaerobic bio-digester module, wherein the anaerobic bio-digester module is configured to digest the organic waste, wherein the digestion of the organic waste produces biogas and biodigestate;
 (2) a nutrient recovery module, wherein the nutrient recovery module is configured to separate a liquid separate from the biodigestate;
 (3) an enclosed bio-production module, wherein the enclosed bio-production module is configured to biologically convert a feedstock to a bio-product, wherein the feedstock comprises liquid separate from the nutrient recovery module; and
 (4) an SRM module, wherein the SRM module is configured to receive animal offal, neutralize at least one pathogen contained within the animal offal, and produce disinfected animal offal, and wherein the organic waste comprises the disinfected animal offal.

30. The facility of claim 29, further comprising an organic waste generator module, wherein organic waste is produced.

31. The facility of claim 30, wherein the cattle feedlot module is configured to receive a feed and produces organic waste comprising manure.

32. The facility of claim 30, wherein the organic waste comprises animal offal.

33. The facility of claim 29, further comprising a gas cleaner module, wherein the gas cleaner module is configured to remove contaminants from the biogas to produce cleaned biogas.

34. The facility of claim 29, further comprising a control system in communication with all of the modules, wherein the control system is configured to monitor the facility and to adjust operating characteristics of the facility.

35. An integrated, modular facility for processing organic waste, wherein the organic waste comprises embedded hard particulates, and the facility comprises:
 (1) an anaerobic bio-digester module, wherein the anaerobic bio-digester module is configured to digest the organic waste, wherein the digestion of the organic waste produces biogas and biodigestate;
 (2) a nutrient recovery module, wherein the nutrient recovery module is configured to separate a liquid separate from the biodigestate;
 (3) an enclosed bio-production module, wherein the enclosed bio-production module is configured to biologically convert a feedstock to a bio-product, wherein the feedstock comprises liquid separate from the nutrient recovery module; and
 (4) a waste processing module, wherein the waste processing module receives the organic waste, removes the embedded hard particulates, and dilutes the organic waste with a diluent.

36. The facility of claim 35, wherein the diluent comprises biodigestate.

37. The facility of claim 35, wherein the waste processing module comprises a waste disruptor and a segregator, and wherein the waste disruptor disrupts the organic waste to release at least one of the disrupted hard particulates, and the segregator segregates the released hard particulates before the organic waste is diluted with a diluent.

38. The facility of claim 35, further comprising an organic waste generator module, wherein organic waste is produced.

39. The facility of claim 38, wherein the cattle feedlot module is configured to receive a feed and produces organic waste comprising manure.

40. The facility of claim 38, wherein the organic waste comprises animal offal.

41. The facility of claim 35, further comprising a gas cleaner module, wherein the gas cleaner module is configured to remove contaminants from the biogas to produce cleaned biogas.

42. The facility of claim 35, further comprising a control system in communication with all of the modules, wherein the control system is configured to monitor the facility and to adjust operating characteristics of the facility.

43. An integrated, modular facility for processing organic waste, the facility comprising:
 (1) an anaerobic bio-digester module, wherein the anaerobic bio-digester module is configured to digest the organic waste, and wherein the digestion of the organic waste produces biogas and biodigestate;
 (2) a gas cleaner module, wherein the gas cleaner module is configured to recover at least one nutrient from the biogas; and,
 (3) an enclosed bio-production module, wherein the enclosed bio-production module is configured to biologically convert a feedstock to a bio-product and a by-product; and wherein the enclosed bio-production module comprises an algal incubator module, and wherein the bio-product comprises lipids.

44. The facility of claim 43, further comprising a nutrient recovery module, wherein the nutrient recovery module is configured to separate the biodigestate, wherein the separation of the biodigestate produces a liquid separate and a solid separate.

45. The facility of claim 43, further comprising an organic waste generator module, wherein organic waste is produced.

46. An integrated, modular facility for processing organic waste, the facility comprising:
 (1) an anaerobic bio-digester module, wherein the anaerobic bio-digester module is configured to digest the organic waste, and wherein the digestion of the organic waste produces biogas and biodigestate;
 (2) a gas cleaner module, wherein the gas cleaner module is configured to recover at least one nutrient from the biogas; and,
 (3) an enclosed bio-production module, wherein the enclosed bio-production module is configured to biologically convert a feedstock to a bio-product and a by-product; and wherein the bio-production module is a bio-diesel production facility and the bio-product comprises bio-diesel fatty acids, wherein the bio-diesel production facility comprises:
  (a) an algal incubator configured to biologically convert the feedstock into lipids; and
  (b) a bio-diesel plant, wherein the biodiesel plant is configured to convert the lipids into bio-diesel fatty acids.

47. The facility of claim 46, wherein the organic waste generator module comprises a cattle feedlot module, wherein the cattle feedlot module is configured to receive a feed and produces organic waste comprising manure.

48. The facility of claim 46, further comprising a nutrient recovery module, wherein the nutrient recovery module is configured to separate the biodigestate, wherein the separation of the biodigestate produces a liquid separate and a solid separate.

49. The facility of claim 46, further comprising an organic waste generator module, wherein organic waste is produced.

50. An integrated, modular facility for processing organic waste, the facility comprising:
(1) an enclosed bio-production module, wherein the enclosed bio-production module is configured to biologically convert a feedstock to a bio-product and a by-product, wherein the enclosed bio-production module comprises an algal incubator module, and wherein the bio-product comprises lipids; and,
(2) an anaerobic bio-digester module, wherein the anaerobic bio-digester module is configured to digest the organic waste and the by-product, and wherein the digestion of the organic waste and the by-product produces biogas and biodigestate.

51. The facility of claim 50, further comprising a nutrient recovery module, wherein the nutrient recovery module is configured to separate the biodigestate, wherein the separation of the biodigestate produces a liquid separate and a solid separate.

52. The facility of claim 50, further comprising an organic waste generator module, wherein organic waste is produced.

53. The facility of claim 52, wherein the organic waste generator module comprises a cattle feedlot module, wherein the cattle feedlot module is configured to receive a feed and wherein organic waste comprising manure is produced therein.

54. An integrated, modular facility for processing organic waste, the facility comprising:
(1) an enclosed bio-production module, wherein the enclosed bio-production module is configured to biologically convert a feedstock to a bio-product and a by-product, wherein the bio-production module is a bio-diesel production facility and the bio-product comprises bio-diesel fatty acids, wherein the bio-diesel production facility comprises:
 (a) an algal incubator configured to biologically convert the feedstock into lipids; and
 (b) a bio-diesel plant, wherein the biodiesel plant is configured to convert the lipids into bio-diesel fatty acids; and,
(2) an anaerobic bio-digester module, wherein the anaerobic bio-digester module is configured to digest the organic waste and the by-product, and wherein the digestion of the organic waste and the by-product produces biogas and biodigestate.

55. The facility of claim 54, further comprising a nutrient recovery module, wherein the nutrient recovery module is configured to separate the biodigestate, wherein the separation of the biodigestate produces a liquid separate and a solid separate.

56. The facility of claim 54, further comprising an organic waste generator module, wherein organic waste is produced.

57. A method for processing organic waste in an integrated, modular facility comprising:
(1) digesting the organic waste in an anaerobic bio-digester module to produce biogas and biodigestate;
(2) separating a liquid separate from the biodigestate in a nutrient recovery module; and
(3) biologically converting a feedstock to a bio-product in an enclosed bio-production module, wherein the feedstock comprises liquid separate from the nutrient recovery module, the biologically converting step comprises growing algae with the feedstock, the enclosed bio-production module comprises an algal incubator module, and the bio-product comprises lipids.

58. The method of claim 57, wherein the biologically converting step further comprises producing algal products as a by-product, and the anaerobic bio-digester module is further configured to digest the algal products, wherein the digestion of the algal products produces biogas and biodigestate.

59. The method of claim 57, further comprising producing organic waste in an organic waste generator module.

60. The method of claim 59, wherein the producing organic waste step comprises producing organic waste in a cattle feedlot module, and wherein the cattle feedlot module is configured to receive a feed and produces organic waste comprising manure.

61. The method of claim 59, wherein the organic waste further comprises animal offal.

62. The method of claim 57, further comprising removing contaminants from the biogas in a gas cleaner module to produce cleaned biogas.

63. A method for processing organic waste in an integrated, modular facility comprising:
(1) digesting the organic waste in an anaerobic bio-digester module to produce biogas and biodigestate;
(2) separating a liquid separate from the biodigestate in a nutrient recovery module; and
(3) biologically converting a feedstock to a bio-product in an enclosed bio-production module, wherein the feedstock comprises liquid separate from the nutrient recovery module, and wherein the biologically converting step comprises:
 (a) growing algae with the feedstock in an algal incubator to produce lipids; and
 (b) transesterifying the lipids in a biodiesel plant to produce bio-diesel fatty acids, wherein the enclosed bio-production module comprises the algal incubator and the bio-diesel plant, and wherein the bio-product comprises bio-diesel fatty acids.

64. The method of claim 63, wherein the biologically converting step further comprises producing glycerol as a by-product, and the anaerobic bio-digester module is further configured to digest the glycerol, wherein the digestion of the glycerol produces biogas and biodigestate.

65. The method of claim 63, further comprising producing organic waste in an organic waste generator module.

66. The method of claim 65, wherein the producing organic waste step comprises producing organic waste in a cattle feedlot module, and wherein the cattle feedlot module is configured to receive a feed and produces organic waste comprising manure.

67. The method of claim 65, wherein the organic waste further comprises animal offal.

68. The method of claim 63, further comprising removing contaminants from the biogas in a gas cleaner module to produce cleaned biogas.

69. A method for processing organic waste in an integrated, modular facility comprising:
(1) digesting the organic waste in an anaerobic bio-digester module to produce biogas and biodigestate;
(2) separating a liquid separate from the biodigestate in a nutrient recovery module; and
(3) biologically converting a feedstock to a bio-product in an enclosed bio-production module, wherein the feedstock comprises liquid separate from the nutrient recovery module, and wherein the biologically converting step comprises fermenting the feedstock, the enclosed bio-production module comprises a fermentation facility and the bio-product comprises ethanol.

70. The method of claim 69, wherein the biologically converting step further comprises producing thin stillage and wet distiller's grains as by-products, and the anaerobic bio-digester module is further configured to digest at least one of the thin stillage and wet distiller's grains, wherein the digestion of the thin stillage and wet distiller's grains produces biogas and biodigestate.

71. The method of claim 69, further comprising removing contaminants from the biogas in a gas cleaner module to produce cleaned biogas and recovering at least one nutrient from the biogas in the gas cleaner module.

72. The method of claim 71, wherein the at least one nutrient comprises ammonia.

73. The method of claim 69, further comprising removing contaminants from the biogas in a gas cleaner module to produce cleaned biogas and transferring the cleaned biogas to a natural gas transmission network.

74. The method of claim 69, further comprising removing contaminants from the biogas in a gas cleaner module to produce cleaned biogas and combusting a fuel in a co-generator module to produce heat and electricity, wherein the fuel comprises cleaned biogas.

75. The method of claim 74, wherein the fuel comprises biogas.

76. The method of claim 74, further comprising transferring the electricity to an electric power transmission network.

77. The method of claim 74, further comprising transferring at least one of the heat and the electricity to the anaerobic bio-digester module.

78. The method of claim 69, further comprising producing organic waste in an organic waste generator module.

79. The method of claim 78, wherein the producing organic waste step comprises producing organic waste in a cattle feedlot module, and wherein the cattle feedlot module is configured to receive a feed and produces organic waste comprising manure.

80. The method of claim 78, wherein the organic waste further comprises animal offal.

81. The method of claim 69, further comprising removing contaminants from the biogas in a gas cleaner module to produce cleaned biogas.

82. A method for processing organic waste in an integrated, modular facility comprising:
(1) digesting the organic waste in an anaerobic bio-digester module to produce biogas and biodigestate;
(2) separating the a liquid separate from the biodigestate in a nutrient recovery module;
(3) biologically converting a feedstock to a bio-product in an enclosed bio-production module, wherein the feedstock comprises liquid separate from the nutrient recovery module;
(4) neutralizing at least one pathogen contained within animal offal in an SRM module; and
(5) producing disinfected animal offal, wherein the organic waste comprises the disinfected animal offal.

83. The method of claim 82, further comprising producing organic waste in an organic waste generator module.

84. The method of claim 83, wherein the producing organic waste step comprises producing organic waste in a cattle feedlot module, and wherein the cattle feedlot module is configured to receive a feed and produces organic waste comprising manure.

85. The method of claim 83, wherein the organic waste further comprises animal offal.

86. The method of claim 82, further comprising removing contaminants from the biogas in a gas cleaner module to produce cleaned biogas.

87. A method for processing organic waste in an integrated, modular facility, wherein the organic waste comprises embedded hard particulates, said method comprising:
(1) removing the embedded hard particulates in a waste processing module;
(2) diluting the organic waste with a diluent in the waste processing module;
(3) digesting the organic waste in an anaerobic bio-digester module to produce biogas and biodigestate;
(4) separating a liquid separate from the biodigestate in a nutrient recovery module; and
(5) biologically converting a feedstock to a bio-product in an enclosed bio-production module, wherein the feedstock comprises liquid separate from the nutrient recovery module.

88. The method of claim 87, wherein the diluent comprises biodigestate.

89. The method of claim 87, wherein the waste processing module comprises a waste disruptor and a segregator, and wherein the method further comprises:
(1) disrupting the organic waste in the waste disruptor to release at least one of the disrupted hard particulates; and
(2) segregating the released hard particulates with the segregator before the organic waste is diluted with a diluent.

90. The method of claim 87, further comprising producing organic waste in an organic waste generator module.

91. The method of claim 90, wherein the producing organic waste step comprises producing organic waste in a cattle feedlot module, and wherein the cattle feedlot module is configured to receive a feed and produces organic waste comprising manure.

92. The method of claim 90, wherein the organic waste further comprises animal offal.

93. The method of claim 87, further comprising removing contaminants from the biogas in a gas cleaner module to produce cleaned biogas.

94. A method for processing organic waste in an integrated, modular facility comprising:
(1) digesting the organic waste in an anaerobic bio-digester module to produce biogas and biodigestate;
(2) recovering at least one nutrient from the biogas in a nutrient recovery module;
(3) biologically converting a feedstock to a bio-product and a by-product in an enclosed bioproduction module, wherein the biologically converting step comprises growing algae with the feedstock, the enclosed bio-production module comprises an algal incubator module, and the bio-product comprises lipids.

95. The method of claim 94, further comprising separating the biodigestate in a nutrient recovery module, wherein the separation of the biodigestate produces a liquid separate.

96. The method of claim 94, further comprising producing organic waste in an organic waste generator module.

97. The method of claim 96, wherein the producing organic waste step comprises producing organic waste in a cattle feedlot module, wherein the cattle feedlot module is configured to receive a feed and produces organic waste comprising manure.

98. A method for processing organic waste in an integrated, modular facility comprising:
(1) digesting the organic waste in an anaerobic bio-digester module to produce biogas and biodigestate;
(2) recovering at least one nutrient from the biogas in a nutrient recovery module;

(3) biologically converting a feedstock to a bio-product and a by-product in an enclosed bioproduction module, and wherein the biologically converting step comprises:
   (a) growing algae with the feedstock in an algal incubator to produce lipids; and
   (b) transesterifying the lipids in a biodiesel plant to produce bio-diesel fatty acids, wherein the enclosed bio-production module comprises the algal incubator and the bio-diesel plant, and wherein the bio-product comprises bio-diesel fatty acids.

99. The method of claim 98, further comprising separating the biodigestate in a nutrient recovery module, wherein the separation of the biodigestate produces a liquid separate.

100. The method of claim 98, further comprising producing organic waste in an organic waste generator module.

101. A method for processing organic waste in an integrated, modular facility comprising:
   (1) biologically converting a feedstock to a bio-product and a by-product in an enclosed bioproduction module, wherein the biologically converting step comprises growing algae with the feedstock, the enclosed bio-production module comprises an algal incubator module, and the bio-product comprises lipids; and
   (2) digesting the organic waste and the by-product in an anaerobic bio-digester module to produce biogas and biodigestate.

102. The method of claim 101, further comprising separating the biodigestate in a nutrient recovery module, wherein the separation of the biodigestate produces a liquid separate.

103. The method of claim 101, further comprising producing organic waste in an organic waste generator module.

104. The method of claim 103, wherein the producing organic waste step comprises producing organic waste in a cattle feedlot module, wherein the cattle feedlot module is configured to receive a feed and organic waste comprising manure is produced therein.

105. A method for processing organic waste in an integrated, modular facility comprising:
   (1) biologically converting a feedstock to a bio-product and a by-product in an enclosed bioproduction module; wherein the biologically converting step comprises:
      (a) growing algae with the feedstock in an algal incubator to produce lipids; and
      (b) transesterifying the lipids in a biodiesel plant to produce bio-diesel fatty acids, wherein the enclosed bio-production module comprises the algal incubator and the bio-diesel plant, and wherein the bio-product comprises bio-diesel fatty acids, and
   (2) digesting the organic waste and the by-product in an anaerobic bio-digester module to produce biogas and biodigestate.

106. The method of claim 105, further comprising separating the biodigestate in a nutrient recovery module, wherein the separation of the biodigestate produces a liquid separate.

107. The method of claim 105, further comprising producing organic waste in an organic waste generator module.

* * * * *

UNITED STATES PATENT AND TRADEMARK OFFICE
CERTIFICATE OF CORRECTION

PATENT NO. : 7,927,491 B2
APPLICATION NO. : 12/004927
DATED : April 19, 2011
INVENTOR(S) : Mike Kotelko et al.

It is certified that error appears in the above-identified patent and that said Letters Patent is hereby corrected as shown below:

On Title Page, item [75], Inventors should read as follows:

Inventors:

Mike Kotelko, Vegreville (CA);

Trevor Jason Nickel, Hairy Hill (CA);

Bern Kotelko, Vegreville (CA);

Brett Kotelko, Edmonton (CA);

Xiaomei Li, Edmonton (CA)

Signed and Sealed this
Twenty-fourth Day of May, 2011

David J. Kappos
*Director of the United States Patent and Trademark Office*